United States Patent [19]

Arnost et al.

[11] Patent Number: 5,034,317

[45] Date of Patent: Jul. 23, 1991

[54] ENZYME CONTROLLED RELEASE SYSTEM AND ORGANIC CONJUGATE REACTANT

[75] Inventors: Michael J. Arnost, North Andover; Frank A. Meneghini, Arlington; Paul S. Palumbo, West Newton, all of Mass.

[73] Assignee: Polaroid Corporation, Cambridge, Mass.

[21] Appl. No.: 8,939

[22] Filed: Jan. 30, 1987

[51] Int. Cl.$^5$ .............................................. C12Q 1/34
[52] U.S. Cl. ......................................... 435/18; 435/4; 435/19; 435/21; 435/14; 435/6
[58] Field of Search .................. 435/4, 18, 14, 19, 21, 435/6

[56] References Cited

U.S. PATENT DOCUMENTS

| | | |
|---|---|---|
| 3,443,939 | 5/1969 | Bloom et al. |
| 3,443,940 | 5/1969 | Bloom et al. |
| 3,751,406 | 8/1973 | Bloom |
| 3,980,479 | 9/1976 | Fields et al. |
| 4,139,379 | 2/1979 | Chasman et al. |
| 4,318,846 | 3/1982 | Khanna et al. |
| 4,351,760 | 9/1982 | Khanna et al. |
| 4,423,143 | 12/1983 | Rubenstein et al. |
| 4,439,356 | 3/1984 | Khanna et al. |
| 4,447,527 | 5/1984 | Monte et al. |
| 4,469,797 | 9/1984 | Albarella ........................... 435/4 |
| 4,501,692 | 2/1985 | Gibbons et al. |
| 4,629,695 | 12/1986 | Svendven ........................... 435/4 |
| 4,637,988 | 1/1987 | Hinshaw et al. .................. 436/800 |
| 4,906,749 | 3/1990 | Theodoropulos .................. 435/4 |

FOREIGN PATENT DOCUMENTS

WO86/04681 8/1986 PCT Int'l Appl.

OTHER PUBLICATIONS

Raiford et al., "Benzoxazolone Formation in the Attempt to Prepare Certain Mixed Diacyl Derivatives of o-Aminophenol," J. Amer. Chem. Soc., 56: 1586 (1934).
Hutchins et al., "Fast Intramolecular Nucleophilic Attack by Phenoxide Ion on Carbamate Ester Groups," J. Amer. Chem. Soc. 95:7 (1973).

Primary Examiner—Sam Rosen
Attorney, Agent, or Firm—Gaetano D. Maccarone

[57] ABSTRACT

The present invention provides an enzyme controlled release system and prepared reactant by which an identifiable molecule may be released on demand through the action of an active enzyme. The controlled release system is useful for detection of an analyte of interest present in a test sample in picogram per liter quantities and may be employed in a variety of different modes of use including immunoassays, enzyme amplification systems and the release of pharmacologically active ligands.

17 Claims, No Drawings

ENZYME CONTROLLED RELEASE SYSTEM AND ORGANIC CONJUGATE REACTANT

FIELD OF THE INVENTION

The present invention is concerned with systems for the controlled release of an identifiable molecule on demand and is particularly concerned with enzyme controlled release systems which employ an intramolecular displacement reaction mechanism for the release of a specific ligand.

BACKGROUND OF THE INVENTION

Compounds and systems for the controlled release of a specific ligand have been the subject of considerable research and product development for a variety of different applications For example, enzymes and enzyme-conjugates are well recognized reactants in immunoassays for reaction with specific substrates by which a variety of different chromophoric and fluorescent dyes are released. These enzymes and enzyme-conjugates are utilized in mobile and immobilized formats in which the rate of enzymatic reaction and/or the concentration of enzyme reaction product provides qualitative and quantitative data. Illustrative of such enzyme release systems are U.S. Pat. Nos. 4,423,143; 4,501,692; 4,318,846; 4,351,760; 4,439,356; 4,447,527; and 4,481,136.

Alternatively, non-enzymatic release systems are also conventionally known, a representative example being displacement reaction mechanisms and release systems used in photographic processes for the release of color-imaging compounds. Such compounds, in the presence of oxidized color developing agents, typically undergo an intramolecular displacement reaction to form a new heterocyclic ring; and as a function of such displacement reaction mechanism and ring formation, split off mobile and diffusible color-imaging material. Such non-enzyme release systems and compositions reflect the pioneer work of Messrs. Raiford and Inman [*J. Amer. Chem. Soc.* 56:1586 (1934)]and Messrs. Hutchins and Fife [*J. Amer. Chem. Soc.* 95:7 (1973)]; illustrative examples of the displacement reaction release mechanism as it relates to photographic processes and compositions are described in U.S. Pat. Nos. 3,443,939; 3,443,940; 3,751,406; 3,980,479; and 4,139,379.

Despite the ongoing innovations and developments in each of these respective technical areas, there has been no overlap or merger of these individual controlled release techniques. Although the benefits and advantages of such a potential merger between enzymes and compositions able to undergo an intramolecular displacement reaction are substantial, there has not been any innovative development bridging the gap between these technical areas insofar as is presently known.

SUMMARY OF THE INVENTION

An enzyme controlled release system is provided for the release of an identifiable ligand comprising an active enzyme able to cleave a covalently bonded substrate from an organic conjugate composition; and an organic conjugate composition able to react with the enzyme having the formula

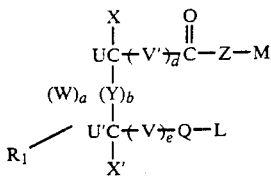

wherein a, b, d, and e individually are 0 or 1;

W may be omitted entirely but when present comprises the number of atoms necessary to form a saturated or an unsaturated cyclic moiety;

X and X' individually are hydrogen, a hydrocarbon entity or a substituted hydrocarbon entity;

Y may be omitted entirely but when present comprises from 1-5 carbon atoms;

U and U' individually are hydrogen or a second covalent bond;

V and V' may be omitted individually or jointly, but when present individually are

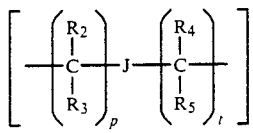

where p is an integer from 0-3,
t is an integer from 0-3, the sum of p+t is from 0-3,
J is

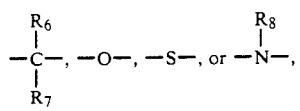

and $R_2$, $R_3$, $R_4$, $R_5$, $R_6$, $R_7$, $R_8$ individually are hydrogen, an alkyl group having from 1-6 carbons or an aryl group;

Q is O, S, NH or NR', R' being an organic entity.

Z is O, S, NH or NR', R' being an organic entity;

L is an enzyme substrate which is cleavable by the active enzyme;

M is any organic moiety without limitation;

$R_1$ is hydrogen or a substituent affecting the mobility or reactivity of the conjugate composition;

and wherein Z-M is the identifiable fragment released in anionic, neutral, or cationic form by intramolecular displacement reaction from the organic conjugate composition after enzymatic cleavage of L.

DETAILED DESCRIPTION OF THE PREFERRED EMBODIMENTS

The present invention is an enzyme controlled release system which uniquely combines at least one enzyme with a prepared organic conjugate composition able to undergo an intramolecular displacement reaction after enzymatic cleavage of a covalently bonded enzyme substrate from the organic conjugate. The controlled release system thus comprises a series of successive chemical events summarized most generally by Reactions I and II below, wherein the neighboring group Q is seen in its anionic form.

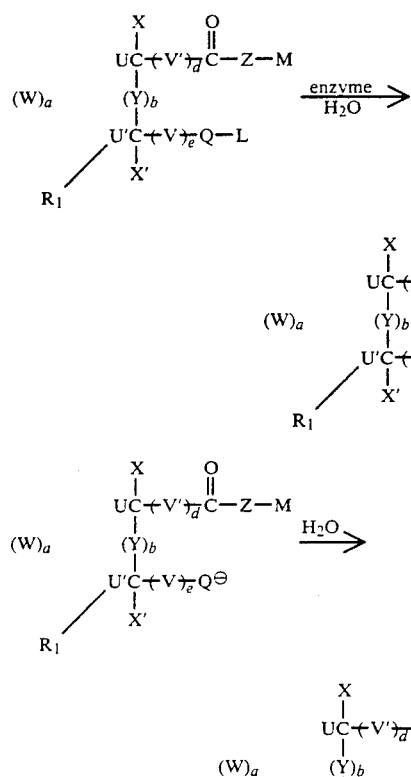

(I)

(II)

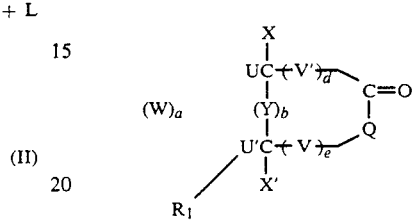

wherein a, b, d, and e individually are 0 or 1;

W may be omitted entirely but when present comprises the number of atoms necessary to form a saturated or unsaturated cyclic molecule;

X and X' individually are hydrogen, a hydrocarbon entity or a substituted hydrocarbon entity;

Y may be omitted entirely but when present is a hydrocarbon comprising from 1-5 carbon atoms;

U and U' individually are hydrogen or a second covalent bond;

V and V' may be omitted individually or jointly, but when present individually are

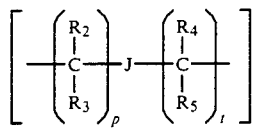

where p is an integer from 0-3,
t is an integer from 0-3, and the sum p+t is an integer from 0-3, and where

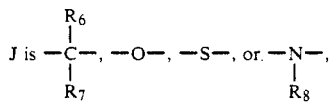

and $R_2$, $R_3$, $R_4$, $R_5$, $R_6$, $R_7$, $R_8$, individually are hydrogen, an alkyl group having 1-6 carbon atoms, or an aryl group;

Q is O, S, NH, or NR', R' being an organic moiety;

Z is O, S, NH, or NR', R' being an organic entity;

L is an enzyme substrate which is cleaved by an active enzyme;

M is an organic moiety without limitation;

$R_1$ is hydrogen or a substituent affecting the mobility and reactivity of the conjugate composition; whereby an identifiable fragment Z-M is released in anionic, neutral, or cationic form by intramolecular displacement reaction from the organic conjugate composition after enzymatic cleavage of L;

and whereby a reaction product represented by the formula is formed, the heterocyclic ring of the fused ring system being not less than 5 atoms and not more than 9 atoms in size.

As stated, Reaction 1 provides the broadest definition of the reactants and clearly relies upon the selective ability of the active enzyme employed to combine with an enzyme substrate L forming a component part of the organic conjugate composition and to specifically cleave the L-Q bond. For this reason, enzymes useful for this purpose within the controlled release system will be described in detail.

The Enzyme

Enzymes having the specific activity to selectively cleave the covalent bond joining the substrate L to the neighboring group Q are conventionally recognized and described in the literature as hydrolases, oxo-reductases, and the like. The user is presumed to have sufficient familiarity with and knowledge of enzyme reactions, enzyme kinetics, and enzyme specificity thereby making the individual choice of substrates, co-factors, reaction conditions and resulting products merely one of personal preference or convenience. Specific details and descriptions of enzymes and enzyme reactions are available in Dixon and Webb, *Enzymes*, Academic Press, 1979; and Dawson, Elliott, and Jones, *Data for Biochemical Research*, 3rd edition, Clarendon Press, 1986, the texts of which are expressly incorporated by reference herein. A representative, but incomplete, listing of individual enzymes suitable for use with specific choices of Q and L which are deemed to be useful when practicing the present invention are given in Table 1 below.

TABLE 1

| Enzyme | Q | L |
|---|---|---|
| Alkaline phosphatase | O | $PO_3^{-2}$ |
| Acid phosphatase | O | $PO_3^{-2}$ |
| β-D-galactosidase | O | β-D-galactose |
| α-D-mannosidase | O | α-D-mannose |
| β-D-glucosidase | O | β-D-glucose |
| β-D-fructofuranosidase | O | β-D-fructofuran |
| thioglucosidase | S | glycosyl residue |
| Bovine trypsin | NH | CBZ-glycine-arginine |

TABLE 1-continued

| Enzyme | Q | L |
| --- | --- | --- |
| Leucineaminopeptidase | NH | leucine |
| Snake venom phosphodiesterase | O | adenosine-5'-phosphate |
| Pancreatic ribonuclease | O | cytidine-3'-phosphate |

The enzyme chosen for use in the controlled release system may be employed in several formats: as an unjoined enzyme; as an enzyme conjugated to a ligand of known composition or activity; as a mobile molecule in either unjoined or conjugated form; and as an immobilized molecule in either unjoined or conjugated form.

As an unjoined entity, the enzyme chosen need only demonstrate a measurable and reproducible degree of specific activity characterized by the ability to combine with an enzyme substrate L and to selectively cleave the covalent bond joining L to the neighboring group Q.

In the conjugated enzyme format, the chosen enzyme is joined in a conventional manner to a ligand having specific properties. Common examples of such ligands are: one of a specifically binding pair of immunological reactants, typically antigens and their specific antibodies; specific binding proteins such as biotin and avidin; and hormones and their target organs. Methods for conjugating ligands to enzymes without substantial loss or modification of the enzyme's specific activity are illustrated by U.S. Pat. Nos. 4,423,143 and 4,501,692. Other such useful techniques (in a homogeneous enzyme immunoassay context) are described in U.S. Pat. Nos. 4,376,825; 4,282,325; 4,203,802; 4,067,774; 3,852,157; 4,190,496; and 4,191,613 respectively.

As regards the immobilization of either unjoined or conjugated enzymes, the specific manner and chemical reaction means by which the enzyme is attached to a solid phase surface or carrier may be selected from those presently available to meet the user's needs or convenience. Such immobilization techniques and processes by which the unjoined enzyme or conjugated enzyme is attached directly or via the use of "linker-arms" to solids such as plastic and latex, test tubes, discs, agarose and plastic beads, porous glass, and polyacrylamide gels are described in: *Methods In Enzymology*, Academic Press, 1980; Updike, *Antibiotics And Chemotherapeutics* 26:67 (1979); and U.S. Pat. Nos. 3,793,445; 3,970,429; and 4,138,474.

In its most general form, the organic conjugate composition reactant of Reaction 1 is

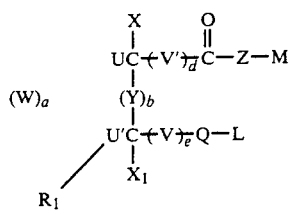

where V, V', Y, U, U', X, X', Q, L, Z, M, and $R_1$ are as previously defined herein. As is apparent from this general structure, the prepared reactant comprises three requisite components and provides an optional fourth component. These are: an organic base supporting structure, $$(W)_a$$
$$X'-U'C-(Y)_b-UC-X;$$

a primary enzyme-sensitive appendage comprising a variable entity $-V-_3$, a masked neighboring group Q, and a masking enzyme substrate L bound in sequence to the organic base structure; a secondary displacement appendage comprising a variable entity $V'_d$, a carbonyl group, and a displaceable fragment Z-M bound in sequence to the base structure; and an optional organic moiety $R_1$ through which the rate of Reactions I and II may be modulated or through which the prepared reactant may be immobilized or solubilized. Each of these component parts will be described in detail.

The Organic Base Supporting Structure

The supporting structure of the prepared reactant is based upon the presence of an organic base structure having at least two carbon atoms available for the attachment of other appendages and which are not distanced from each other by more than 5 atoms. The base supporting structure may comprise saturated and unsaturated molecules, straight and branched linear chains, single and multiple rings, and include a variety of heterocyclic ring structures. Each of these base structures may also contain substituted hydrocarbons and organic groups known in the art. A representative, but incomplete, listing of organic base structures deemed to be useful in the present invention is provided by Table 2 below.

TABLE 2

| Organic Base | base structure | organic conjugate composition |
| --- | --- | --- |
| phenyl ring and phenyl derivatives | 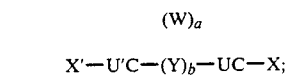 | |

TABLE 2-continued

| Organic Base | base structure | organic conjugate composition |
|---|---|---|
| Napthalene and derivatives | [decalin with R$_1$] | [decalin with L—Q—(V)$_e$ and (V')$_d$—C(=O)—Z—M substituents, R$_1$] |
| Quinoline and derivatives | [decahydroquinoline with R$_1$, NH] | [decahydroquinoline with R$_1$, NH, (V')$_d$—C(=O)—Z—M, (V)$_e$—Q—L] |
| Indole and derivatives | [indoline-type structure with NH] | [indoline-type structure with NH, (V')$_d$—C(=O)—Z—M, (V)$_e$—Q—L] |
| phenanthrene and derivatives | [phenanthrene skeleton with R$_1$] | [phenanthrene skeleton with R$_1$, L—Q—(V)$_e$, (V')$_d$—C(=O)—Z—M] |
| cyclohexane | [cyclohexane with R$_1$] | [cyclohexane with R$_1$, (V')$_d$—C(=O)—Z—M, (V)$_e$—Q—L] |
| dicyclohexane | [decalin with R$_1$] | [decalin with R$_1$, (V')$_d$—C(=O)—Z—M, (V)$_e$—Q—L] |
| norbornane and derivatives | [norbornane] | [norbornane with V—Q—L and V'—CO—Z—M substituents, subscripts e and d] |

TABLE 2-continued

| Organic Base | base structure | organic conjugate composition |
|---|---|---|
| butane | CH₃–CH₂–CH₂–CH₃ (branched structure shown) | CH₂(V')$_d$C(=O)–Z–M / CH₂–CH₂ / CH₂(V)$_e$Q–L |
| cis-2-pentene | CH₂–CH₃ / CH=CH–CH₃ | CH₂–CH₂(V')$_d$C(=O)–Z–M / CH=CH–CH₂(V)$_e$Q–L |
| cis,cis-2,4-hexadiene | CH=CH–CH₃ / CH / CH=CH–CH₃ | CH–CH₂(V')$_d$C(=O)–Z–M / CH / CH=CH–CH₂(V)$_e$Q–L |

The Primary Enzyme-Sensitive Appendage

The primary enzyme-sensitive appendage is a linear sequence represented as
—V$_e$—Q—L The variable entity V₃ (e being 1 or 0) when present

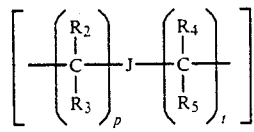

where p is an integer from 0-3,
t is an integer from 0-3, the sum of p+t is an integer from 0-3, and

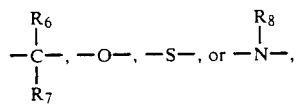

and R₂, R₃, R₄, R₅R₆, R₇, and R₈, individually ar hydrogen, and alkyl group having from 1-6 carbons, or an aryl group. Clearly, the maximum length for V is four carbon atoms in size. In preferred embodiments, however, e is zero and V is omitted entirely from the appendage sequence.

Q is selected from the group consisting of oxygen, sulfur, nitrogen and substituted nitrogen groups; in preferred embodiments Q is an oxygen atom. L is an enzyme substrate which is attached by covalent bonds to Q and while in this state serves to mask (or block) the chemical reactivity of Q. L is chosen in accordance with the specific activity of the enzyme to be employed in the release system. A representative listing of substances useful as L has been given by Table 1 previously.

It will be appreciated by practitioners ordinarily skilled in this art that the primary enzyme-sensitive appendage sequences comprise some elements which are relatively unrestricted in size and composition; clearly the masking enzyme substrate L is limited only with respect to the existence of a corresponding active enzyme able to react with it. In comparison, the composition of V and Q in combination is limited to a known set of specific entities; moreover the size of V and Q together can not be less than 1 atom and not more than 5 atoms in length.

The techniques and reactions by which V and Q and L are joined in sequence to the supporting base structure are conventionally known and need not be described in detail herein. It is required that the masking enzyme substrate L be such that the corresponding active enzyme is able to bind with the substrate L and to cleave those covalent bonds joining the substrate L to the neighboring group Q given suitable conditions for reaction (pH, temperature, necessary co-factors, and the like). The kinetics of Reaction I and the disposition of the cleaved substrate L are of no consequence so long as these factors do not substantially interfere with the consequential intramolecular displacement mechanism of Reaction II or the release of the identifiable ligand for the purposes of the particular application.

The event of enzymatically cleaving the masking substrate L from the organic conjugate composition in accordance with Reaction I serves to unmask (deblock) the neighboring group Q. Once unmasked, the presence of the neighboring group Q is the direct initiator of an intramolecular displacement reaction within the secondary displacement appendage, thereby causing the release of an identifiable fragment Z-M and the formation of a heterocyclic ring in accordance with Reaction II. While the particulars of the mechanism by which an anchimerically assisted, intramolecular displacement reaction is initiated (as a result of enzymatically cleaving the substrate L from the organic conjugate composition) is of theoretical interest to practitioners in this art, the individual details regarding the mechanism of action do not themselves limit or restrict the subject matter as a whole comprising the present invention. Accordingly, so long as at least one enzyme is employed to cleave a masking enzyme substrate L from the linkage sequence (V)$_e$Q—L comprising part of an organic conjugate composition with the consequence that an intramolecular displacement reaction is initiated and an identifiable fragment is released, that embodiment is deemed to be within the scope of the present invention.

The Secondary Displacement Appendage

A requisite part of the prepared reactant is a secondary linear displacement appendage represented as

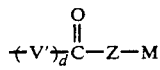

The variable entity $V'_d$ (d being 1 or 0), can be omitted entirely but when present is

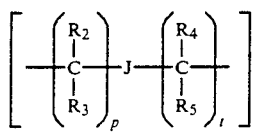

wherein p is an integer from 0-3,
t is an integer from 0-3, and the sum of p+t is an integer from 0-3; and wherein

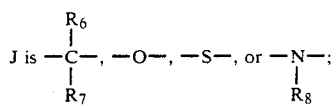

and $R_2$-$R_8$ individually are hydrogen, an alkyl group having from 1-6 carbon atoms, or an aryl group. In preferred embodiments V' is —$NR_8$—.

Z is selected from the group consisting of oxygen, sulfur, nitrogen or a substituted nitrogen group NR'; where R' is an organic entity. M is any organic moiety without limitation and is chosen in accordance with the desired application.

A critical feature of the prepared reactant is that after the occurrence of an initiating enzyme reaction (Reaction I), the secondary displacement appendage sequence becomes subject to an intramolecular displacement reaction such that the Z-M portion of the appendage is actually displaced (i.e. released into the surrounding environment). Furthermore, as a result of this intramolecular displacement reaction, a heterocyclic ring is formed.

The selection of the displaceable fragment Z-M will vary directly with the properties and characteristics of the ligand desired to be released, and thus is a function of the intended application. It is expected that the displaceable fragment Z-M will take the form of a chromophoric, fluorescent, or chemiluminescent dye; a dye precursor; a specific amino acid such as serine, cysteine, tyrosine, lysine, glutamic acid; or be a biologically active species-as for example drugs, steroids, polypeptides or proteins which permit them to be attached to the appendage without substantially affecting the biological properties of the molecule as a whole. This last category particularly includes polypeptides of recognized specific activity such as enzymes; polypeptides able to bind specifically to another molecule such as hormones; and polypeptides having defined pharmacological properties such as tissue plasminogen activator (tPA). A representative, but incomplete, listing of entities suitable for use as M in conjunction with various choices of Z is presented in Table 3.

TABLE 3

| Displaceable ligand (Z—M) | HZ—M Structure | Z | Category of Use |
|---|---|---|---|
| Ortho-nitrophenol | OH, NO2 (on cyclohexane ring) | —O— | chromophoric dye |
| Para-nitrophenol | OH, NO2 (para on cyclohexane ring) | —O— | chromophoric dye |
| Phenolphthalein | (phenolphthalein structure) | —O— | chromophoric dye |
| β-naphthol (2-hydroxynaphthalene) | (naphthol structure with OH) | —O— | dye coupler; chromophoric dye (via diazonium salt) |

TABLE 3-continued

| Displaceable ligand (Z—M) | HZ—M Structure | Z | Category of Use |
|---|---|---|---|
| Naphthionic acid (1-naphthylamine-4-sulfonic acid) | [naphthalene with SO₃H at 1-position and NH₂ at 4-position] | —NH— | chromophoric dye (via diazotized phenyl salt) |
| Umbelliferone (7-hydroxycoumarin) | [7-hydroxycoumarin structure] | —O— | fluorescent dye |
| 4-methyl umbelliferone | [4-methyl-7-hydroxycoumarin structure] | —O— | fluorescent dye |
| resorufin | [resorufin structure] | —O— | fluorescent dye |
| Lysine | residue—C(=O)—CH(NH-residue)—CH₂—CH₂—CH₂—CH₂—NH₂ | —NH— | Amino acid in a polypeptide chain |
| Arginine | residue—C(=O)—CH(NH-residue)—CH₂—CH₂—CH₂—N—C(=NH)—NH₂ | —NH— | Amino acid in a polypeptide chain |
| Tyrosine | residue—C(=O)—CH(NH-residue)—CH₂—(phenyl)—OH | —O— | Amino acid in a polypeptide chain |
| Serine | residue—C(=O)—CH(NH-residue)—CH₂—OH | —O— | Amino acid in a polypeptide chain |

TABLE 3-continued

| Displaceable ligand (Z—M) | HZ—M Structure | Z | Category of Use |
|---|---|---|---|
| Cysteine | residue—C(=O)—CH(—NH—residue)—CH₂—SH | —S— | Amino acid in a polypeptide chain |
| Cortisone | 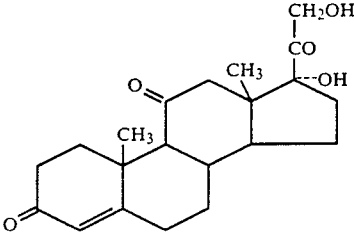 | —O— | Steroid |

The Anchimerically Assisted, Intramolecular Displacement Reaction

Intramolecular reactions are analogous to bimolecular (intermolecular) reactions in which two discrete reactants combine to form one or more end products, but differ enormously in their individual rates of reaction. The rate of a bimolecular reaction such as $$RCO_2R' + R''NH_2 \rightarrow RCONHR'' + R'OH$$

is expressed as a second order equation whose rate is dependent upon the initial concentration of the two reactants, $RCO_2R'$ and $R''NH_2$ respectively. However, if the same two reactants comprise component parts of a single large molecule, an intramolecular reaction becomes possible and the rate can be reduced to a first order equation. In addition, if certain electronic and sterochemical parameters are controlled, the driving energy forces favoring such an intramolecular displacement become large and the rate of intramolecular cyclization can far exceed the rate of reaction for the analogous bimolecular (intermolecular) reaction. In those instances where the intramolecular displacement reaction is accelerated in rate via the presence of a neighboring group whose sterochemical and electronic characteristics are well defined (such as neighboring group Q of the present invention), such intramolecular reactions are said to be anchimerically assisted because the displacement and cyclization proceeds through what is, in effect, an internally attached form of the reactants. Such anchimercially assisted reactions often exhibit very rapid rates of reaction with rate factors of $10^3-10^4$ being commonly observed.

The pertinent literature in this art has recognized the general characteristics of intramolecular reactions and identified many factors influencing intramolecular catalysis, anchimeric assistance, and the formation of ring systems. These include: Hutchins & Fife, *J. Am. Chem. Soc.* 95:2282 (1973); Morris & Page, *J. Chem. Soc., Perkins* 11:679 (1980); T. H. Fife, *Advanced Physical Organic Chemistry*, Volume 11 (Gold & Bethell, editors), Academic Press, New York, 1975, pp. 5-19 and 39-60; B. Capon & S. P. McManus, *Neighboring Group Participation*, Plenum Press New York, 1976, pp. 43-71 and 182-187; and E. L. Eliel, *Sterochemistry Of Carbon Compounds*, McGraw-Hill Book Co. Inc., New York, 1962, pp. 198-203, the texts of which are expressly incorporated by reference herein.

Clearly important factors to be considered are the nature of the nucleophilic and displacing groups, ring size, electronic and sterochemical influences, substituent effects, strain energy and entropic effects. The present invention utilizes these factors to effect fast intramolecular displacement of an identifiable fragment from a precursor conjugate reactant under carefully controlled conditions. In simpler terms, the organic conjugate composition described herein can properly be thought of as means for the cyclic joining together of two functional appendages within the same molecule by way of controlled intramolecular displacement. This is made possible by use of a strong nucleophilic, neighboring group Q having sufficient activation energy to initiate displacement and cyclization; by masking (or blocking) the activity of the nucleophilic neighboring group Q with a masking (or blocking) enzyme substrate L which can be cleaved at will by addition of a suitable enzyme; and by prior selection, control and adjustment of the intramolecular reactants and structural geometry such that the two reactive partners are in the appropriate orientation one to the other Control of the masking (blocking) enzyme substrate L therefore allows for control over the entire anchimerically assisted intra molecular displacement reaction. This is best demonstrated by individually describing some of the preferred embodiments.

Embodiment A

If the base supporting structure for the organic conjugate composition takes the form of an aryl base represented generally as

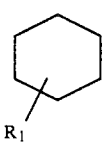

the prepared reactant will react in conformity with Reactions III and IV below.

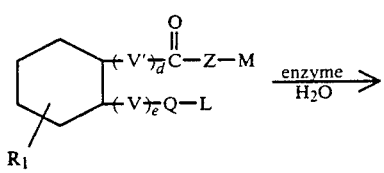

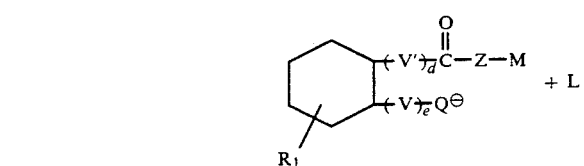

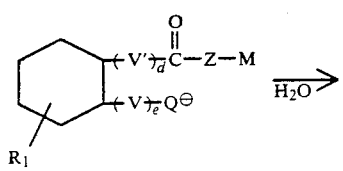

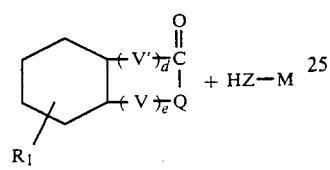

where V, V', Z, M, Q, L and $R_1$ are as previously defined herein.

Clearly, the primary enzyme sensitive appendage $V_eQ$—L lies ortho and in a cis orientation with respect to the secondary displacement appendage $V'_dCO$—Z—M. The proximity and steric constraint is provided by the benzene ring structure and the adjacent positioning of the respective appendages on the benzene ring without any intervening atoms between them. Similarly, the available degrees of rotational freedom are reduced such that a reactive sterochemical position is maintained intramolecularly. After cleavage of the masking substrate L by the appropriate enzyme (Reaction III), the neighboring group Q is unmasked and functions as a nucleophile to initiate displacement of the Z-M moiety (Reaction IV). The size of the ring formed by Reaction IV is carefully controlled to be within specified limits and comprises a minimum of 5 atoms and a maximum of only 9 atoms.

This size limitation as to the number of atoms in the heterocyclic ring is best visualized by the minimal and maximal forms. Recognizing that both V and V' cannot be omitted concurrently in this embodiment and keeping V (or V') to the minimal one atom in size, the reaction product yielded is the minimal situation where the heterocyclic ring contains 5 atoms. Alternatively, if both V and V' are present and take the largest of the permissible forms, the resulting product is the maximal permissible situation in which 9 atoms comprise the newly formed heterocyclic ring.

Embodiment B

If the base supporting structure for the organic conjugate composition takes the form of a bicyclic aromatic ring such as

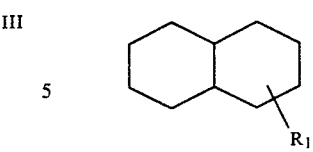

the prepared conjugate reactant will act in conformity with Reactions V and VI below.

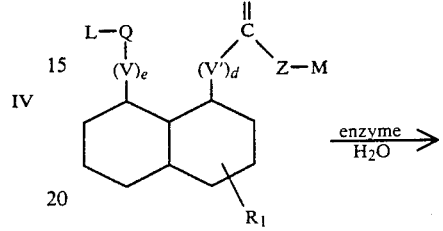

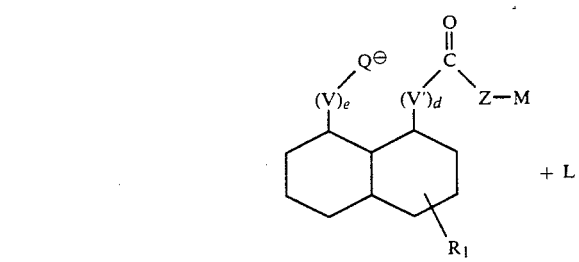

where V, V', Q. L, Z, M and $R_1$ as previously defined.

Embodiment B illustrates the situation where there is one carbon atom separating the primary enzyme-sensitive appendage from the secondary displacement appendage at their respective points of attachment to the bicyclic base structure.

Reaction V demonstrates the enzymatic control over the masking group L which when cleaved unmasks (deblocks) the nucleophile $Q^-$ to initiate Reaction VI. The size of the heterocyclic ring formed is held to be within carefully controlled limits of not less than 5 atoms and not more than 9 atoms in size. The number of carbon atoms (3) in the bicyclic base between the respective appendages permits both V and V' to be entirely omitted and still meet the minimal required ring size of 5 atoms. Alternatively, where both V and V' are present, the reaction products can be the maximal compositional size of 9 atoms.

Embodiment C

If the base supporting structure for the organic conjugate composition takes the form of a linear (straight or branched) saturated hydrocarbon such as $$R-CH_3-CH_2-CH_2-CH_2-CH_2-R'$$

where R and R' are hydrogen or an organic entity, the prepared conjugate reactant will act in conformity with Reactions VII and VIII below.

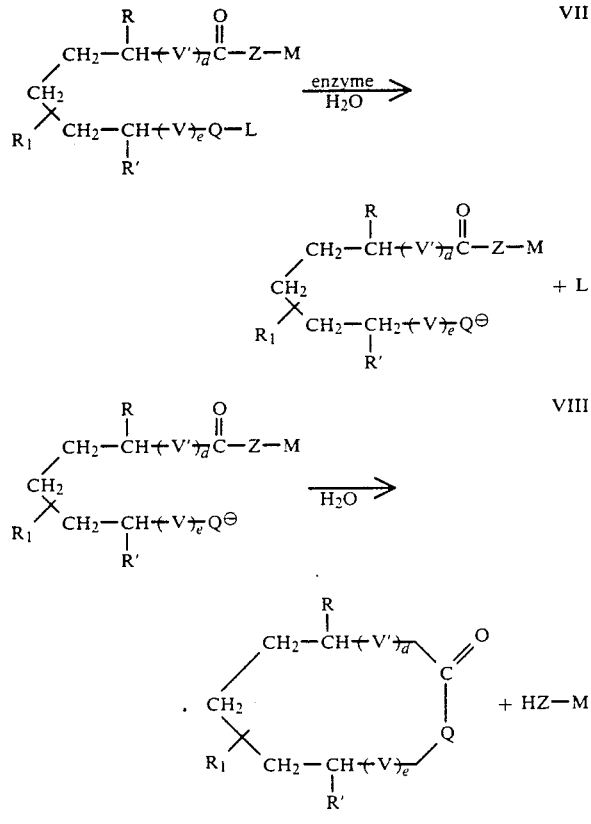

where V, V', Q, L, M, Z, and $R_1$ are as previously described.

Embodiment C illustrates the permissible situation where Y is a 3 carbon atom linkage. Clearly, in comparison with Embodiments A and B reactant C presents the least favorable embodiment for molecular displacement and cyclization. The proximity distance is large; there is no steric constriction provided by the base structure; and the largest number of degrees of rotational freedom are available. These less desirable features will markedly reduce the rate of Reaction VIII to be the slowest among Embodiments A-C. However, there is no doubt whatsoever that Reactions VII and VIII will occur so long as the selection of V, V', Q, conform to the previously defined forms.

Accordingly, the number of carbon atoms (5) in the linear base between the respective appendages narrows the possible choices of V and V' to comprise a maximum of 2 atoms in size yielding the maximal 9 atom ring size. On the other hand, if both V and V' are omitted entirely, the minimal 7 atom heterocyclic ring is formed.

Optional $R_1$ Moiety

It is recognized and expected that in many applications, the prepared organic conjugate composition will be employed either in an immobilized form or a freely mobile format. One provision for immobilizing the organic conjugate composition is made via the $R_1$ moiety which is used to join the organic conjugate to a solid surface or carrier. A wide variety of different alkyl and aryl compositions and reactions are conventionally known for this purpose. Particularly useful as immobilizing linkages are compositions comprising the piperizinyl sulfonyl series represented as

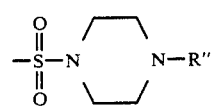

where each R" is hydrogen or a lower alkyl radical bonded directly to the solid surface or carrier. Other immobilizing linkages deemed to be useful are described in Example 5 which follows herein. Alternatively, the $R_1$ moiety will increase the mobility of the organic conjugate composition as a whole in a fluid. An illustrative embodiment of the $R_1$ moiety able to increase mobility is the succinylated piperazinyl sulfonyl group described in Example 15 hereinafter. It should be understood that the $R_1$ moiety can be used to modulate the reactivity of the conjugate composition. For example, when the $pK_a$ of Q is important in reactions I and II, those reactions can be accelerated by suitable choice of $R_1$.

To ensure a clear and complete understanding of the enzyme controlled release system, the reactants employed, their manner of use, and the reactions responsible for the release of an identifiable ligand, the following Examples describing the synthesis and use of one preferred embodiment

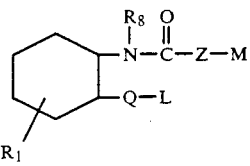

are provided. It will be expressly understood, however, that the particulars of the components comprising each of the reactants, the nature of the identifiable ligand released, the specific enzyme employed, and the conditions of use are not limiting or restrictive of the invention in any way or manner. To the contrary, it is expected and intended that the user will freely choose among the many compounds and constituents presently known and available commercially in this art for his reactants, his choice of enzyme, the specific ligand to be released, and the precise conditions for use, all of which will vary with the intended application and the needs of the user.

EXAMPLE 1

Synthesis of 2-[N-ethyl N-carbo (p-nitrophenoxy)]-4-dimethylamino sulfonyl phenyl-β-D-galactopyranoside.

The preparation of the aryl conjugate composition, 2-[N-ethyl-N-carbo (p-nitrophenoxy)]4-dimethylamino sulfonylphenyl-β-D-galactopyranoside, proceeds according to the following reaction Scheme I.

REACTION SCHEME I

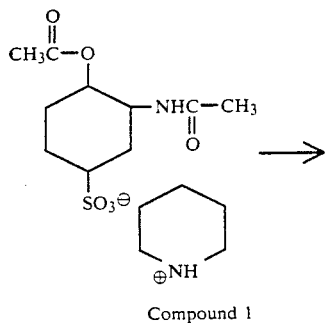

Compound 1

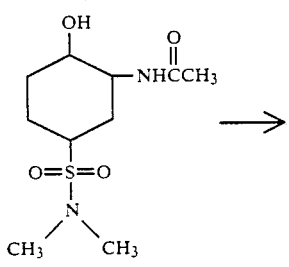

Compound 2

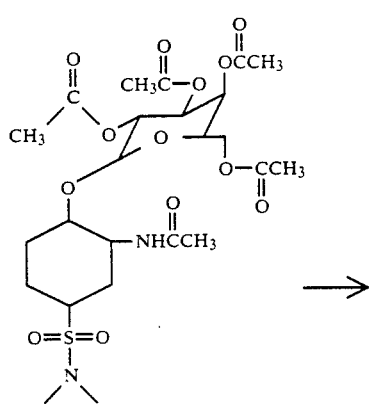

Compound 3

-continued
REACTION SCHEME I

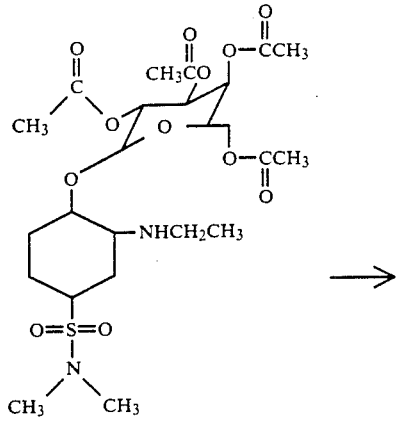

Compound 4

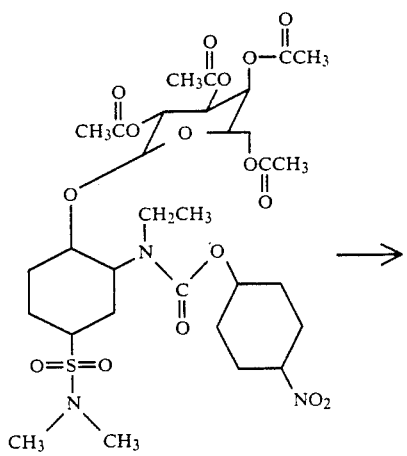

Compound 5

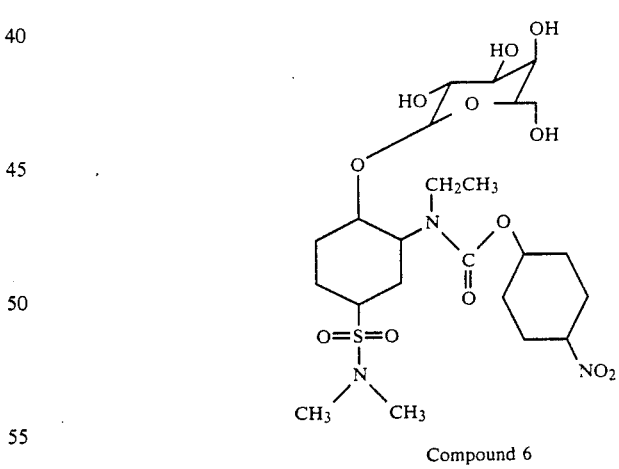

Compound 6

Initially a stirred mixture comprising 10.0 grams (0.028 moles) of compound 1 [Williams, R. T., *J. Chem. Soc.* 708 (1942)] and 5.3 milliliters (hereinafter "ml") of phosphorous oxychloride in 100 ml of methylene chloride ($CH_2Cl_2$) was refluxed under a calcium chloride drying tube for 4 hours. The resulting solution was cooled to room temperature, allowed to stand overnight, and then added dropwise with stirring to 100 ml of cold water. The aqueous and organic layers formed in this manner were separated and the organic layer treated with 50 ml of aqueous dimethylamine (25% in water). This mixture was vigorously stirred for 4 hours and the resulting two-phase mixture cooled in ice and then acidified with concentrated HCl to approximately pH 4. A precipitate results which is isolated by suction filtration, washed five times consecutively with water and then dried to yield 3.62 grams (50%) of a fine white solid-compound 2. [$^1$H-NMR(d-6 DMSO/CDCl$_3$): δ2.2 (s,3H); 2.65 (s,6H); 6.95 (d, J=9 Hz, 1H); 7.33 (dd, J$_1$=9 Hz, J$_2$=2.5, 1H); 8.2 (d, J=2.5 Hz); 9.1 (bs, 1H) 10.6 (bs, 1H); MS (258 M+)].

The next step utilizes a prepared mixture comprising 1.0 grams (3.87 millimoles) of compound 2, 0.88 grams (3.87 millimoles) of benzyltriethyl ammonium chloride and 0.77 grams (19.0 millimoles) sodium hydroxide in 15 ml of CH$_2$Cl$_2$ and 5.0 ml of water. This prepared mixture was vigorously stirred at room temperature and was treated in a single portion with 1.6 grams (3.87 millimoles) of 2, 3, 4, 6-tetra-0-acetyl-α-D-galactopyranosyl bromide (Sigma Corporation). The resulting two phase mixture was stirred continuously for six hours, followed by the addition of 0.8 grams (1.94 millimoles) of the α-bromo-tetra-acetyl-D-galactose, and stirred continuously overnight. Subsequently, the organic and aqueous phases (layers) were separated and the organic phase dried over sodium sulfate and evaporated in vacuo. The resulting residue was subjected to liquid chromatography using a silica column (Silica Woelm 32-63) and an eluent comprising 1.0% of CH$_3$OH in CH$_2$Cl$_2$ to yield 0.8 grams (35%) of compound 3. [$^1$H NMR (CDCl$_3$): δ2 (s, 3H); 2.03 (s, 3H); 2.1 (s, 3H); 2.15 (s, 3H); 2.2 (s, 3H); 2.65 (s, 6H); 4.15 (bs, H); 5.1–5.55 (m, 4H); 7.03 (d, J=9 Hz, 1H); 7.35 (dd, J$_1$=9 Hz, J$_2$=2.5 Hz, 1H); 7.93 (bs, 1H); 8.73 (d, J=2.5 Hz, 1H); IR (CH$_2$Cl$_2$) 3400 (b), 1760, 1750, 1745 cm$^{-1}$; M.S. (M+588)].

Subsequently, a solution comprising 0.705 grams (1.2 mmole) of compound 3 in 40 ml of tetrahydrofuran (hereinafter "THF") was made and placed under an atmosphere of nitrogen with constant stirring. To this stirred solution 1.32 ml (2.6 mmole) borane-dimethyl sulfide solution (2M in THF) was added dropwise at room temperature. The resultant mixture was stirred overnight at room temperature and then refluxed for approximately one-half hour. The liquid mixture was then cooled to room temperature, treated with 1.0 ml of acetic acid, and then evaporated to dryness in vacuo. The formed residue was subjected to liquid chromatography using a silica column with an eluent comprising 1.0–3.0% CH$_3$OH in CH$_2$Cl$_2$. 0.27 grams (39%) of compound 4 was obtained as a solid foam upon removal of effluent from the appropriate fractions and high vacuum evaporation [$^1$H NMR (CDCl$_3$): δ1.30 (t, J=7 Hz, 3H); 2.05–2.2 (3 singlets, 12H); 2.74 (s, 6H); 3.23 (q, J=7 Hz, 2H); 4.1–4.3 (m, 3H); 5.0–5.7 (m, 4H); 6.9–7.1 (m, 3H)].

The synthesis continues by combining 13.0 mg (0.023 mmole) of compound 4 with 3.5 ul (0.025 mmole) of triethylamine in 1.0 ml of THF and treating this mixture in a single portion with 5.0 mg (0.025 mmole) p-nitrophenyl-chloroformate, under an atmosphere of nitrogen (N$_2$). The reaction mixture was stirred overnight at room temperature, suction filtered, and the filtrate evaporated to dryness. The resulting residue was subjected to liquid chromatography using a silica column with a 1% CH$_3$OH/CH$_2$Cl$_2$ eluent to yield 10.0 mg (60%) of compound 5 [$^1$H NMR (CDCl$_3$): δ1.2 (m, 3H); 1.5–2.2 (3 major singlets, 2 minor broad singlets, total of 12H); 3.5–4.0 (m, 2H); 4.0–4.4 (m, 3H); 5.1–5.6 (m, 4H); 7.1-7.6 (m, 3H); 7.65-7.8 (m, 2H); 8.2-8.4 (m, 2H)].

Reaction scheme I is completed by preparing a mixture comprising 0.334 grams (0.452 mmol) of compound 5 and 3.1 ml (22.6 mmol) of triethylamine in 35 ml of methanol. This mixture was stirred at room temperature for approximately 8.5 hours and then evaporated to dryness under high vacuum overnight. The resulting residue was subjected to liquid chromatography using a silica column with an eluent comprising 10% CH$_3$OH in CH$_2$Cl$_2$.

The effluent after high vacuum evaporation provided 0.165 grams (64%) of compound 6 as a solid foam [$^1$H NMR (CD$_3$OD/CDCl$_3$): δ1.2 (t, J=7 Hz, 3H); 2.75 (s, 6H); 3.3–4.1 (complex multiplet, 12H); 5.0 (m, 1H); 7.2–7.5 (m, 3H); 7.6–7.8 (m, 2H); 8.1–8.4 (m, 2H). Analysis calculated for C$_{23}$H$_{29}$N$_3$SO$_{12}$:C, 48.33; H, 5.11; N, 7.35; S, 5.61. Found: C, 47.98; H, 5.20; N, 7.01; S, 5.45].

EXAMPLE 2

Synthesis of 2-[N-ethyl-N-carbo (resorufinyl)]-4-dimeehylamino sulfonylphenyl-β-D-galactopyranoside.

The preparation of the aryl conjugate composition, 2-[N-ethyl-N-carbo (resorufinyl)-4-dimethylamino sulfonyl phenyl-β-D-galactopyranoside, is summarized by Reaction Scheme II below.

REACTION SCHEME II

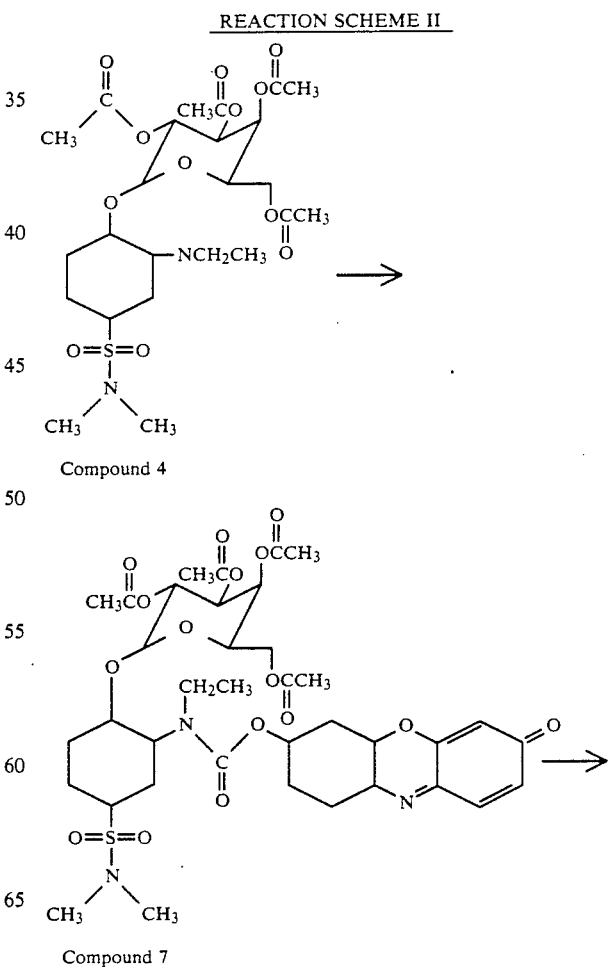

Compound 4

Compound 7

-continued
REACTION SCHEME II

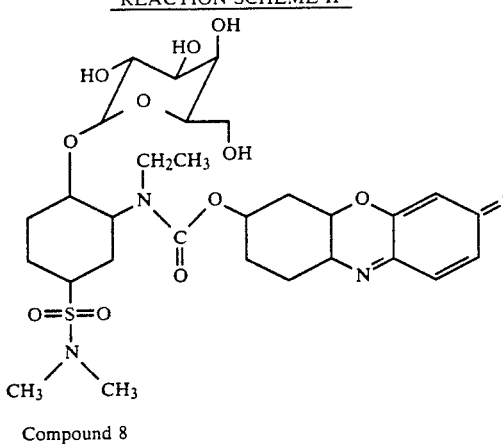

Compound 8

Initially, compounds 1-4 are synthesized in the manner described within Example 1 above. Subsequently, a solution comprising 0.27 grams (0.47 mmol) of compound 4 in 10.0 ml of $CH_2Cl_2$ is added dropwise over 15 minutes to a stirred solution comprising 0.12 ml of phosgene (12.5% solution in benzene) in 10 ml of $CH_2Cl_2$ at a temperature ranging from 0°-5° C. Alternatively, 28 $\mu l$ (0.24 mmole) of trichloromethyl-chloroformate (a phosgene equivalent) and 67 $\mu l$ triethylamine (0.48 mmol) may be used. The reaction mixture is slowly warmed to room temperature and then stirred overnight. Subsequently, the liquid is evaporated in vacuo leaving a colorless solid residue. All of this solid residue is then combined with 0.15 grams (0.71 mmol) resorufin dissolved in 3.0 ml of pyridine at 0°-5° C. The formed liquid mixture is again slowly warmed to room temperature and then is continuously stirred at room temperature for approximately 4 hours. After evaporation of volatile solvent under high vacuum, a residue is formed with is subjected to liquid chromatography using a silica column and an eluent comprising 1.0% $CH_3OH$ in $CH_2Cl_2$. 60 mg (16%) of yellow-orange solid foam was recovered as compound 7 [$^1$H NMR ($CDCl_3$): $\delta 1.25$ (m, 3H); 1.8-2.4 (3 major singlets, 1 minor singlet, 12H); 2.8 (s, 6H); 3.6-4.1 (m, 2H); 4.1-4.4 (m, 3H); 5.1-5.7 (m, 4H); 6.33 (bs, 1H); 6.85 (dd, $J_1=10$ Hz, $J_2=2$ Hz, 1H); 7.0-7.6 (m, 4H); 7.7-7.9 (m, 3H)].

Compound 7 was finally treated with triethylamine in methanol according to the procedure given for preparation of compound 6. Analysis of Compound 7 revealed: [$^1$H NMR ($CD_3OD/CDCl_3$): $\delta 1.2$ (t, $J=7$ Hz, 3H); 2.75 (s, 6H); 3.5-4.1 (m, 12H); 5.0 (m, 1H); 6.35 (bs, 1H); 6.83 (dd, $J_1=10$ Hz, $J_2=2$ Hz, 1H); 7.1-7.5 (m, 4H); 7.6-7.9 (m, 3H). M.S.: (M+646). $\lambda_{max}^{pH7}$ 457 ($\epsilon 10,230$)].

EXAMPLE 3:

Synthesis of the trifluoroacetic acid salt of 2-[N-ethyl-N-carboresorufinyl]-4-piperazinosulfonyl-phenyl-$\beta$-D-galacto pyranoside.

The preparation of the aryl conjugate composition, the trifluoroacetic acid salt of 2-[N-ethyl-N-carboresorufinyl]-4-piperazino-sulfonylphenyl-$\beta$-D-galactopyranoside, is summarized by Reaction Scheme III below.

REACTION SCHEME III

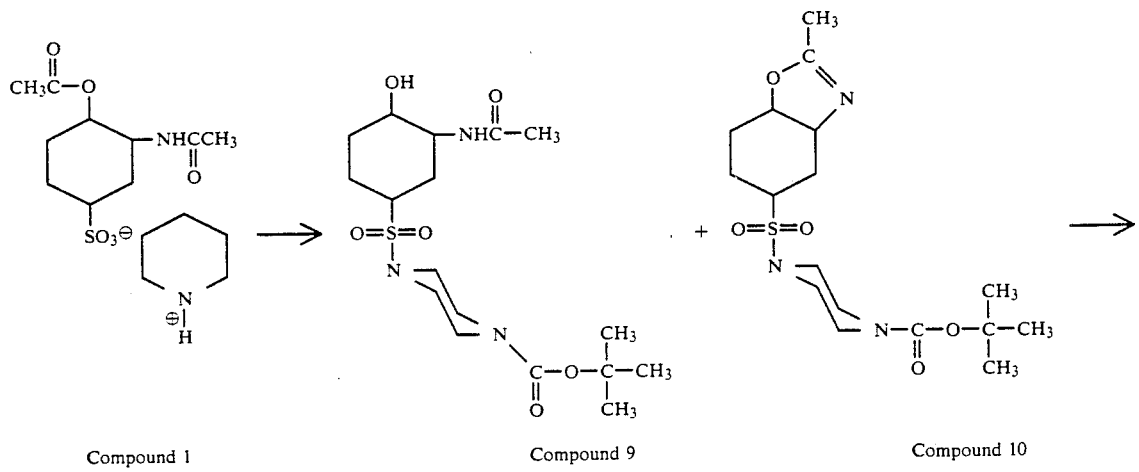

Compound 1    Compound 9    Compound 10

-continued
REACTION SCHEME III

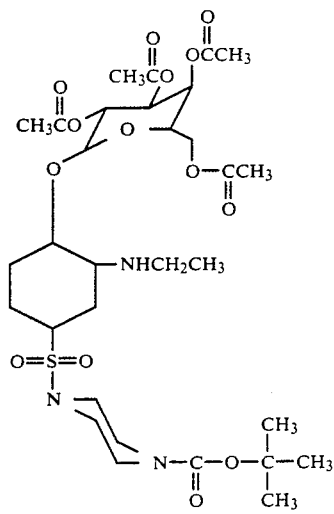

Compound 11

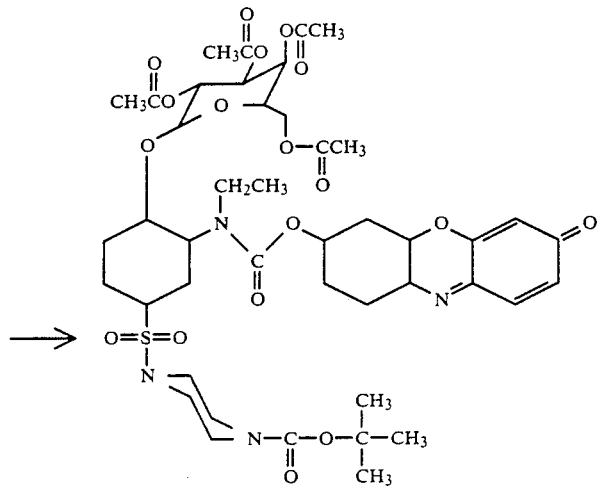

Compound 12

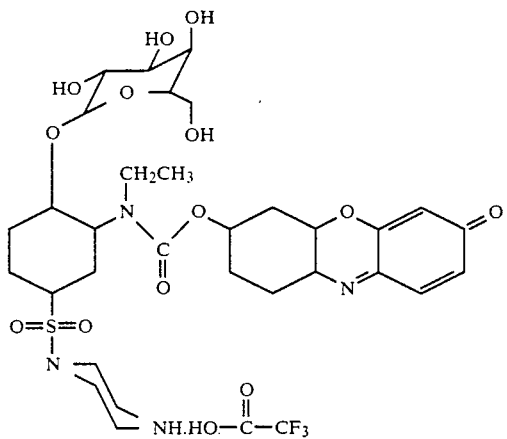

Compound 13

The preparation begins with compound 1 of Example 1 above in which 5.0 grams (0.014 mol) of compound 1 and 2.65 ml of phosphorous oxychloride are combined in 50 ml of CH$_2$Cl$_2$ and refluxed under a calcium chloride drying tube for approximately 4 hours. The resulting solution is cooled to room temperature, allowed to stand at room temperature overnight, and then added dropwise to 100 ml of cold water with continuous stirring. The formed aqueous and organic phases are separated and the organic phase is dried over Na$_2$SO$_4$ (anhydrous) and then added dropwise to a cold solution containing 6.03 grams (0.07 mol) piperazine dissolved in a mixture of 60 ml dimethylformamide (hereinafter "DMF") /20 ml CH$_2$Cl$_2$. This reaction mixture was slowly warmed to room temperature and stirred for 4 hours. Evaporation of the volatile solvent yielded a solid residue which was triturated with CH$_2$Cl$_2$, filtered, and washed with excess CH$_2$Cl$_2$. The isolated filtrate was evaporated in vacuo to yield a crude amber syrup. Subsequently, this crude product was dissolved in a mixture comprising 50 ml CH$_2$Cl$_2$/10 ml DMF and treated dropwise with stirring at room temperature with 8.0 ml (0.035 mol) of di-t-butyl dicarbonate. After allowing the mixture to react for 1.5 hours, the volatiles were removed by high vacuum evaporation to yield a residue. The formed residue was then combined with ethylacetate; washed successively with water and 1 N HCL; dried over anhydrous MgSO$_4$; and again subjected to evaporation. The resulting residue was triturated with diethylether; filtered; and again dried to yield 3.0 grams (54%) of solid comprising a mixture of compound 9 and compound 10.

Subsequently, a solution comprising 3.0 grams (0.0075 mol) of the white solid comprising compounds 9 and 10 respectively and 45 ml of THF was prepared and treated with a dropwise addition of 11.3 ml (0.023 mol) borane-dimethyl sulfide solution (2 M in THF). This reaction mixture was refluxed under nitrogen for two hours. The resultant mixture was then allowed to stand at room temperature overnight followed by cautious quenching with excess absolute ethanol and subsequent evaporation to dryness. The formed residue is then dissolved in excess ethanol and again evaporated in vacuo to dryness to yield a white solid. This white solid reaction production is then combined with 6.2 grams (0.015 mol) of 2, 3, 4, 6-tetra-O-acetyl-α-D-galactopyranosyl bromide, 1.7 grams (0.0075 mol) benzyl triethylammonium chloride, and 37.5 ml (0.011 mol) of 0.3 M NaOH in 40 ml of $CH_2Cl_2$. This biphasic mixture is stirred vigorously at room temperature for approximately three hours. The mixture is then allowed to separate into aqueous and organic phases which were isolated. The aqueous phase is then extracted with another 40 ml of $CH_2Cl_2$. The combined organic phases were then dried over anhydrous $Na_2SO_4$ followed by evaporation under vacuum. The resulting residue is then subjected to liquid chromatography using a silica column and an eluent comprising 1.0% $CH_3OH$ in $CH_2Cl_2$. 4.0 grams (75%) of compound 11 is obtained from the collected effluent. [$^1H$ NMR ($CDCl_3$): δ; 1.25 (t, J=7 Hz, 3H); 1.45 (s, 9H); 2.0 (s, 3H); 2.07 (bs, 6H); 2.15 (s, 3H); 2.8-3.3 (m, 6H); 3.3-3.6 (m, 4H); 4.0-4.4 (m, 3H); 4.9-5.5 (m, 4H); 6.7-6.9 (m, 3H)].

Subsequently, a solution containing 3.33 grams (4.65 mmol) of compound 11 and 0.65 ml (4.65 mmol) of triethylamine in 60 ml THF is added dropwise under nitrogen to a stirred solution of 0.28 ml (2.33 mmol) trichloromethyl chloroformate in 60 ml of THF at a temperature ranging from 0°-5° C. After the addition, the reaction mixture is allowed to warm to room temperature and stirred for approximately one hour. The resulting mixture is then suction filtered; washed with 10 ml of THF; and the filtrate evaporated to dryness. The formed residue is then combined with 1.1 grams (4.65 mmol) resorufin-sodium salt dissolved in 30 ml pyridine and stirred overnight at room temperature. After evaporation of the solvent, the residue is dissolved in excess ethylacetate; then washed successively with water, an aqueous saturated $NaHCO_3$ solution and brine; and then dried over anhydrous $MgSO_4$. Evaporation in vacuo to dryness affords a residue which is subjected to liquid chromatography using a silica column and an eluent comprising 2% $CH_3OH$ in $CH_2Cl_2$. 2.53 grams (57%) of an orange solid is obtained as compound 12. [$^1H$ NMR ($CDCl_3$): δ1.25 (t, J=7 Hz, 3H); 1.45 (s, 9H); 1.7-2.15 (multiple singlets, 12H); 2.9 (m, 4H); 3.4 (m, 4H); 3.5-3.9 (m, 2H); 4.15 (m, 3H); 4.9-5.5 (m, 4H); 6.25 (bs, 1H); 6.75 (dd, $J_1$=10 Hz, $J_2$=2 Hz, 1H); 6.9-7.5 (m, 4H); 7.5-7.8 (m, 3H)].

To complete Scheme III, a mixture containing 2.45 grams (2.57 mmol) of compound 12 and 17.9 ml (128.0 mmol) triethylamine dissolved in 70 ml of methanol is prepared and stirred at room temperature for approximately 7.5 hours. This mixture is then allowed to stand overnight in a freezer. The mixture is allowed to warm to room temperature and is stirred for an additional hour before evaporating under vacuum to dryness The formed residue is dissolved in 70 ml $CH_2Cl_2$; combined with 30 ml of trifluoroacetic acid; and is stirred at room temperature for approximately 10 minutes. The volatile solvent is removed by evaporation. The formed residue was then combined with $CH_2Cl_2$ and evaporated in vacuo several times in sequence. Subsequently, the residue is triturated with 100 ml of $CH_2Cl_2$ containing 10 ml of ethyl ether overnight and then suction filtered to afford 2.0 grams (98%) of an orange powder identified as compound 13 [M.S.: (M+687: free base)].

EXAMPLE 4:

Immobilization of Compound 13 onto Sepharose 4B

A useful solid phase carrier for immobilization of prepared aryl conjugate compositions such as composition 13 are Sepharose gels commercially available from Pharmacia Corporation. A useful immobilization reaction is as follows: 1.0 gram (12 μmol tresyl) of freeze dried tresyl-activated Sepharose 4B was suspended and allowed to swell for several minutes in 1 mM HCl. The swollen gel is then filtered and washed for one hour's duration on a sintered glass filter using a total volume of 200 ml of 1 mM HCl. The washed gel is then vacuum suctioned into a damp filter cake and then transferred to a solution containing 5.0 milligrams (7.0 μmol) of compound 13 in 5.0 ml of phosphate buffer (pH 7.0). This mixture was allowed to stand at room temperature with occasional swirling for approximately 6 hours. Subsequently, the gel is suction filtered on a sintered glass frit, thoroughly washed with phosphate buffer (pH 7.0), followed by additional washing in water. The washed gel is then again suctioned to a damp filter cake. The orange colored gel obtained in this manner comprises immobilized compound 13 but it is preferred that the prepared gel be dialyzed to remove all remaining contaminants prior to use. Accordingly, the orange gel was transferred to dialysis tubing having a 12-14K molecular weight cutoff (Spectraphor membrane tubing, Spectrum Medical Industries) and dialyzed against one liter of distilled water for 3 days with the water being changed every 12 hours. The resulting gel demonstrates a measurable release of resorufin after reaction with *Asp. oryzae* β-galactosidase.

EXAMPLE 5

Useful Immobilization Materials and Reactions

To demonstrate the feasibility of immobilizing the aryl conjugate compositions comprising the present invention, a variety of resorufin containing conjugate reactants were prepared in the manner described within Example 3 to yield the aryl conjugate composition whose structural formula is

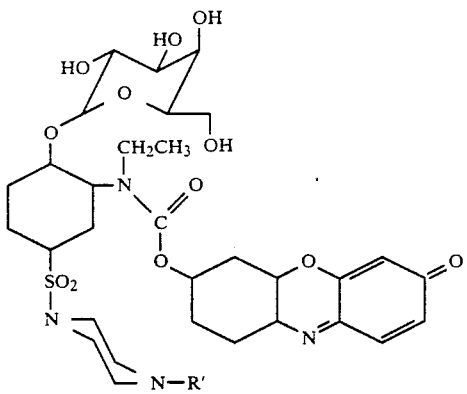

wherein R' is chosen from the group identified below and corresponds to compound 13, 14, or 15 respectively.

| Substance | R' |
|---|---|
| Compound 13 | H.H—O—C—CF$_3$<br>∥<br>O |
| Compound 14 | CH$_3$ |
| Compound 15 | —C—CH$_2$—CH$_2$—COH<br>∥             ∥<br>O             O |

Compounds 13, 14, and 15 respectively may individually be immobilized to a wide variety of different solid support materials and a range of immobilizing reactions conventionally known in this art. Merely to illustrate the variety of solid support carriers and reactions which are deemed useful to prepare immobilized embodiments of the present invention, a summary of different formats and the mobilizing reactions are provided by Tables 4 and 4A respectively.

EXAMPLE 6

The Enzyme Controlled Release System

The release system of the present invention comprising an active enzyme and an aryl conjugate composition comprising a substrate which is open to attack by the enzyme is demonstrated by the interaction between the enzyme Beta-galactosidase in combination with compound 6 described earlier in Example 1; with compound

TABLE 4

| Embodiment | Aryl Conjugate Reactant | Solid Support Material | Immobilizing Reaction | Reaction Conditions |
|---|---|---|---|---|
| A | Compound 13 | Tresyl activated agarose | directly to activated uncrosslinked Sepharose 4B | Room temperature at pH 7.0 for 6 hours |
| B | Compound 13 | Glyoxyl agarose | use of $NaCNBH_3$ as co-reactant aminoalkylation | Room temperature at pH 7.0 for 12 hours |
| C | Compound 13 | Latex beads 0.1$\mu$ diameter | direct bonding with chloromethyl latex at pH 2.0; or $NaCNBH_3$ aldehyde latex as co-reactant at pH 6.0 | Room temperature reactions at pH 2.0 and 6.0 |
| D | Compound 13 | Cellulose carbonate | direct addition reaction to 1000 $\mu$mole/gram of solid | Room temperature at pH 7.0 for 3 hours |
| E | Compound 13 | Tresylagarose | uses excess $H_2N(CH_2)_7CO_2H$ as spacer molecule | Room temperature at pH 7.0 |
| F | Compound 14 | Tresyl activated agarose | direct addition to activated uncrosslinked Sepharose 4B | Room temperature at pH 7.0 for 6 hours |
| G | Compound 14 | Polychloromethyl styrene/polyvinyl alcohol graft latex | direct addition reaction | Reaction at 55° C. at pH 7.0 for 5.5 hours |
| H | Compound 14 | Polychloromethyl styrene/polyvinyl alcohol graft latex | uses glutamic acid as wettable groups | Reaction at 55° C. at pH 7 for 5.5 hours |
| I | Compound 15 | Amino microspheres 0.19$\mu$ diameter | direct addition reaction 3 $\mu$mole/cc or 125 $\mu$mole/gram | Room temperature at pH 7.0 EDCI (ethyl dimethylaminopropyl carbodiimide) |
| J | Compound 15 | Cellulose carbonate | uses excess $H_2N(CH_2)_3N$$N-$ $(CH_2)_3NH_2$ as spacer molecule | Room temperature at pH 11 EDCI (ethyl dimethylaminopropyl carbodiimide) |
| K | Compound 15 | Carboxylate microspheres 0.23$\mu$ diameter | uses excess $H_2N(CH_2)_3N$$N-$ $(CH_2)_3NH_2$ as spacer molecule | In water with EDCI at pH (ethyl dimethylaminopropyl carbodiimide) |
| L | Compound 15 | Tresylagarose | uses excess $H_2N(CH_2)_3N$$N-$ $(CH_2)_3NH_2$ as spacer molecule | Room temperature at pH 7.0 |

It will be appreciated that each of these immobilized embodiments released resorufin in measurable quantities after combination with *Asp. oryzae* $\beta$-galactosidase.

8 described earlier in Example 2; and with ortho-nitro phenyl galactopyranose (hereinafter "ONPC"), commercially available from Sigma CorPoration. The test conditions and kinetic results of enzymatic hydrolysis are summarized in Table 5.

TABLE 5

| Reactant | Reactant Concentration | Temperature | Concentration of Aspergillus oryzae $\beta$-galactosidase | Measured Rate of Reaction | Reaction pH |
|---|---|---|---|---|---|
| ONPG | $10^{-3}M$ | 25 | 0.5 units | 0.038 $\mu$moles/min | 5.5 |
| Compound 6 | $10^{-3}M$ | 25 | 0.5 units | 0.028 $\mu$moles/min | 5.5 |
| ONPG | $10^{-3}M$ | 25 | 1.0 units | 0.15 $\mu$moles/min | 5.5 |
| Compound 6 | $10^{-3}M$ | 25 | 1.0 units | 0.066 $\mu$moles/min | 5.5 |
| ONPG | $10^{-3}M$ | 25 | 0.85 units | 0.022 $\mu$moles/min | 7.0 |
| Compound 6 | $10^{-3}M$ | 25 | 0.85 units | 0.009 $\mu$mole/min | 7.0 |
| ONPG | $10^{-3}M$ | 25 | 4.2 units | 0.087 $\mu$moles/min | 7.0 |
| Compound 6 | $10^{-3}M$ | 25 | 4.2 units | 0.039 $\mu$mole/min | 7.0 |
| ONPG | $1.7 \times 10^{-5}M$ | 36.5 | 0.85 units | 0.012 $\mu$moles/min | 7.0 |
| Compound 6 | $1.7 \times 10^{-5}M$ | 36.5 | 0.85 units | 0.0065 $\mu$mole/min | 7.0 |

TABLE 5-continued

| Reactant | Reactant Concentration | Temperature | Concentration of Aspergillus oryzae β-galactosidase | Measured Rate of Reaction | Reaction pH |
|---|---|---|---|---|---|
| Compound 8 | $1.7 \times 10^{-5}$M | 36.5 | 0.85 units | 0.0015 μmole/min | 7.0 |

EXAMPLE 7

Specificity of the Organic Conjugate Composition

A major advantage provided by the organic conjugate compositions comprising the present invention is the selective ability to discriminate not only between different classes of enzymes, but also to distinguish the same enzyme obtained from different sources. To demonstrate this unique ability, beta-galactosidase derived from *Asperillus oryzae*, beef liver, and *E. coli* were individually evaluated using compounds 6 and 8 respectively as reactants. Each of the individual, separately derived, beta-galactosidases were commercially obtained and empirically evaluated using the test protocol described previously in Example 6. The results of these evaluations are provided by Table 6 below.

TABLE 6

| Temperature | Compound & Concentration | Source of β-galactosidase | Enzyme Concentration | Measured Rate of Reaction | Reaction pH |
|---|---|---|---|---|---|
| 25° C. | $10^{-3}$M cpd 6 | Asp. ory. | 0.5 units | 0.028 μmole/min | 5.5 |
| 25° C. | $10^{-3}$M cpd 6 | beef liver | 0.66 units | 0.0094 μmole/min | 5.5 |
| 25° C. | $10^{-3}$M cpd 6 | Asp. ory. | 0.85 units | 0.0091 μmole/min | 7.0 |
| 25° C. | $10^{-3}$M cpd 6 | beef liver | 0.66 units | 0.00075 μmole/min | 7.0 |
| 25° C. | $10^{-3}$M cpd 6 | E. coli | 7.5 units | 0.00006 μmole/min | 7.0 |
| 36.5° C. | $1.7 \times 10^{-5}$M | Asp. ory. | 0.85 units | 0.0015 μmole/min | 7.0 |
| 36.5° C. | $1.7 \times 10^{-5}$M cpd 8 | beef liver | 0.66 units | incomplete hydrolysis after 4 days | 7.0 |

It is clearly demonstrated that the release of ortho-nitrophenol from compound 6 (and the release of resorufin from compound 8) will vary directly with the individual source of β-galactosidase and that the rate at which the displaceable ligand is released will vary drastically under similar test conditions. The ability of the present invention to identify and discriminate among different sources of the same enzyme is thus unequivocally demonstrated.

EXAMPLE 8

Detection of $1.0 \times 10^{-12}$ M Enzyme

Experimental conditions: Ten microliters of $1.0 \times 10^{-10}$ M *Aspergillus oryzae* Beta galactosidase (Cal Biochem) in 100 mM citrate phosphate, pH 5, with 0.05% w/v gelatin (Buffer A) was added to one milliliter of 1.6 mM compound 15 in Buffer A, yielding a final enzyme concentration of $1.0 \times 10^{-12}$ M. One half milliliter of this reaction mixture was monitored in a spectrofluorimeter in a two millimeter cuvette with instrument settings of 540 nm excitation, 580 emission and 5 nm slit widths. The signal was measured on a chart recorder at a speed of one centimeter per minute and at a sensitivity setting that gave fifteen percent deflection with $1.7 \times 10^{-7}$ M Sulforhodamine 101 in ethanol.

An increase in signal over time was observed with the enzyme reaction mixture and in a ten minute interval there was a one and one half percent increase in deflection. No increase in the signal generated by the substrate solution alone was seen. Accordingly, the detection of $1.0 \times 10^{-12}$ M concentrations of enzyme is deemed to be proven unequivocally.

APPLICATIONS

The enzyme controlled release system and the prepared organic conjugate compositions used as reactants in combination with an active specific enzyme may be beneficially employed in a variety of different modes of application. Different features and characteristics of the invention are utilized to advantage in each of these modes of use. It will be recognized also that the described modes which follow are merely representative of the many other applications for the present invention; and are not in any manner or form restrictive of the present invention to the described modes of use.

Immunoassays for Research or Clinical/Diagnostic Analyses

In this mode, the enzyme is covalently bonded to a ligand having known specific binding properties for an analyte of interest. Typically, there is an analyte analogue employed to provide a competition between the analyte of interest and the analyte analogue for the binding sites of the ligand (the specific binding partner) joined to the enzyme. Frequently, the specific binding partner ligand joined to the enzyme will be a protein or a polypeptide and may functionally be classified as an antibody (of monoclonal or polyclonal origin); or an antibody fragment (such as a Fab fragment or Fab' fragment); or a specific binding molecule (such as avidin or biotin). The analyte of interest demonstrates a specific binding affinity for the ligand attached to the enzyme and is typically identified as an antigen or hapten; a specific binding protein; or a molecule having specific receptor sites for the ligand. The analyte analogue typically is a chemical composition identical or similar to the analyte of interest and is also chosen on the basis of its demonstrated ability to selectively bind to the ligand previously joined to the enzyme. After the interaction of the immunological components, the ligand-enzyme complex is brought into reactive contact with the organic conjugate composition whereby the displaceable fragment Z-M is released. In this manner, the presence and concentration of one or more analytes of interest may be detected with precision and accuracy.

Enzyme Triggered Fluorescence Assays

This mode of use is a general one, but is especially applicable to the immunoassay mode described above. The prepared organic conjugate composition brought into reactive contact with an appropriate active enzyme or the immunological ligand-enzyme complex described previously comprises a Z-M fragment which is a fluorescent dye. While attached to the secondary displacement appendage as a component part of the conjugate reactant, the dye moiety does not exhibit any meaningful fluorescence or exhibits a change in its excitation maxima. The attack of the enzyme or ligand-enzyme complex cleaves the attached enzyme substrate, which, in turn initiates the intramolecular displacement reaction and the release of the fluorescent dye as a mobile entity into the reaction medium. Upon release, and the introduction of light at the appropriate wavelength, the mobile dye will fluoresce and be detectable as such. In this manner, the mode may be employed in either a qualitative or quantitative methodology.

One aspect of the enzyme triggered fluorescent assay mode described herein deserves special attention: the organic conjugate composition comprising the attached fluorescent (or chromophoric, or chemiluminescent) dye as a component part may be employed as either a mobile reactant or as an immobilized reactant joined to a solid carrier. The ability to immobilize a prepared organic conjugate composition comprising a fluorescent dye precursor and subsequently to release from it a mobile fluorescent dye is an important advantage of the present invention.

Analytical Systems Requiring Enzyme Amplification

In many instances where the detection of an enzyme is the goal of the assay, a major drawback of known detection systems is their relative insensitivity and/or inability to provide sufficient quantities of an identifying label with respect to the quantity of enzyme in the test sample. More precisely, although conventional reactants interact with the enzyme in the sample, that quantity of identifying label which is released by the test system as an indication of reactive contact is often insufficient to be measured by the existing instrumentation for the analysis to be accurately made. This is especially true in assays for the detection of specific enzymes which are generally present in nanogram or picogram quantities. The present invention provides for amplification of such detection assays using the release system in series or multiple stages. For example, if the detection of beta-galactosidase were the goal of the assay, a first stage reactant would comprise an immobilized organic conjugate composition comprising a substrate L specific for beta-galactosidase and a displaceable fragment Z-M which is another active enzyme having a broader substrate range, such as amylase. The amylase enzyme molecule would be joined to the immobilized organic base structure by one of its constituent lysine, tyrosine, serine, or thiol residues via its extending side groups. A second stage conjugate composition would also be prepared as a second immobilized reactant in which another attached substrate L would be one open to attack by the displaced amylase enzyme molecule after its release from the first stage reactant. The displaceable fragment Z-M of this second prepared reactant typically would be a measurable dye (chromophoric, chemiluminescent or fluorescent).

In the analytical protocol, the presence of β-galactosidase in the test sample would initiate an attack on the first immobile conjugate reactant and cause the release of the amylase enzyme as the first displaced Z-M fragment; the released amylase would then be able to react with a known concentration of the second organic conjugate composition having its own substrate L open to attack by the released amylase which, in turn, will cause the release of an identifiable dye as the second displaced Z-M fragment. The concentration of the second organic conjugate reactant would typically be much greater than the concentration of the first conjugate reactant to achieve the amplification effect. Accordingly, a single molecule of β-galactosidase (through the two-stage enzyme controlled release system) will cause the release of many molecules of identifiable dye in an amount sufficient to be reproducibly and accurately measured by conventional photometric means. In this manner, the presence of minute quantities of β-galactosidase in the test sample can be amplified using the present invention to achieve positive detection and quantitative measurement.

Release of Specific Agents on Demand

This mode of use is employed when the release of a specific agent is required on demand or is desirable in response to a specific triggering event. Such situations include the release of a therapeutic drug, protein, or pharmacologically active agent; or the release of a molecule having specific properties and characteristics such as a photographic dye. In such situations, the prepared organic conjugate composition will comprise the agent to be released as the displaceable fragment Z-M in the prepared reactant. The addition of an active enzyme able to cleave a substrate L of the conjugate composition will cause the release of the desired displaceable ligand (agent) directly on demand. In this manner, the desired active agent will be in an attached state subject to immediate release upon the introduction of an appropriate active enzyme.

Although the invention has been described with respect to specific preferred embodiments, it is not intended to be limited thereto but rather those skilled in the art will recognize that variations and modifications may be made therein which are within the spirit of the invention and the scope of the appended claims. For example, the organic conjugate composition may comprise a saturated or unsaturated cyclic moiety (a=1) which is substituted with $R_1$. It will be understood by those skilled in the art that the cyclic moiety may be further appropriately substituted with one or more additional substituents which affect the mobility or reactivity of the conjugate composition. Thus, analogs possessing the advantageous features of the conjugate composition according to the invention will be considered as equivalents thereof for the purposes of the claims herein.

What we claimed is:

1. An enzyme controlled release system for the release of an identifiable ligand comprising:
   an active enzyme able to cleave a substrate from an organic conjugate composition; and
   an organic conjugate composition able to react with said enzyme, said organic conjugate composition having the formula

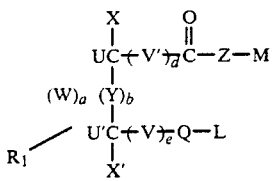

wherein a, b, d, and e individually are 0 or 1;
W may be omitted entirely but when present comprises the number of atoms necessary to form a saturated or unsaturated cyclic molecule;
X and X' individually are hydrogen, a hydrocarbon entity or a substituted hydrocarbon entity;
Y may be omitted entirely but when present comprises from 1-5 carbon atoms;
U and U' individually are hydrogen or a second covalent bond;
V and V' may be omitted individually or jointly, but when present are

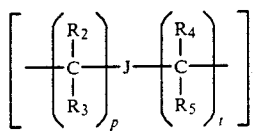

wherein
p is an integer from 0–3,
t is an integer from 0–3, the sum of p+t is from 0–3, and wherein J is

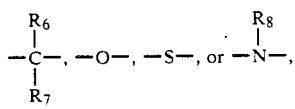

and $R_2$, $R_3$, $R_4$, $R_5$, $R_6$, $R_7$, $R_8$ individually are hydrogen, an alkyl group having from 1-6 carbons or an aryl group;
Q and Z individually are O, S or NH;
L is an enzyme substrate which is cleavable by said enzyme;
M is an organic moiety;
$R_1$ is hydrogen or a substituent affecting the mobility or reactivity of said organic conjugate composition;
and whereby Z-M is an identifiable fragment released by intramolecular displacement reaction from said organic conjugate composition after said enzymatic cleavage of L and upon the removal of Z-M and L;

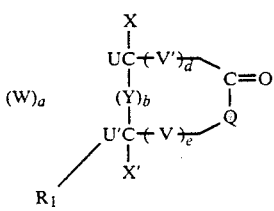

and Q join to form a cyclic reaction product.

2. The release system as recited in claim 1 wherein said organic conjugate composition yields a reaction product comprising a heterocyclic ring, said reaction product having the formula

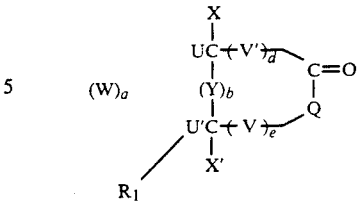

wherein said heterocyclic ring is not less than 5 atoms and not more than 9 atoms in size.

3. An enzyme controlled release system for the release of an identifiable ligand comprising:
an active enzyme able to cleave a substrate from an organic conjugate composition; and
an organic conjugate composition able to react with said enzyme, said organic conjugate composition having the formula

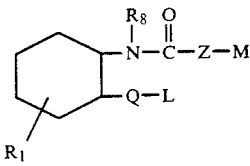

wherein Q and Z individually are O, S or NH;
L is an enzyme substrate which is cleavable by said enzyme;
M is an organic moiety;
$R_1$ is hydrogen or a substituent affecting the mobility or reactivity of said organic conjugate composition;
$R_8$ is an organic substituent; and wherein Z-M is an identifiable fragment released by intramolecular displacement reaction from said organic conjugate composition after said enzymatic cleavage of L and upon the removal of Z-M and L;

and Q join to form a cyclic reaction product.

4. The release system as recited in claim 3 wherein said organic conjugate composition yields a reaction product comprising a heterocyclic ring, said reaction product having the formula

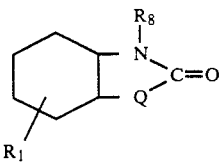

5. The release system as recited in claim 1 or 3 wherein said enzyme is a hydrolase.

6. The release system as recited in claim 1 or 3 wherein said organic conjugate composition comprises a base supporting structure selected from the group consisting of phenyl and phenyl derivatives, naphthalene and naphthalene derivatives, quinoline and quinoline derivatives, indole and indole derivatives, and phenanthrene and phenanthrene derivatives.

7. The release system as recited in claim 1 wherein said organic conjugate composition comprises a base supporting structure selected from the group consisting of saturated and unsaturated cyclic organic compounds.

8. The release system as recited in claim 1 wherein said organic conjugate composition comprises a base supporting structure selected from the group consisting of saturated or unsaturated linear organic compounds.

9. The release system as recited in claim 1 or 3 wherein said identifiable fragment Z-M is a dye or dye precursor.

10. The release system as recited in claim 1 or 3 wherein said identifiable fragment Z-M is a fluorescent dye.

11. The release system as recited in claim 1 or 3 wherein said identifiable fragment Z-M is a chemiluminescent dye.

12. The release system as recited in claim 1 or 3 wherein said identifiable fragment Z-M comprises at least one amino acid.

13. The release system as recited in claim 1 or 3 wherein said identifiable fragment Z-M is an active enzyme.

14. The release system as recited in claim 1 or 3 wherein said identifiable fragment Z-M has specific binding properties for another compound.

15. The release system as recited in claim 1 or 3 wherein said active enzyme is attached to a ligand.

16. The release system as recited in claim 15 wherein said ligand attached enzyme is immobilized to a solid carrier.

17. The release system as recited in claim 15 wherein said ligand attached enzyme is in a mobile state.

* * * * *